US009429637B2

(12) United States Patent
Krueger et al.

(10) Patent No.: US 9,429,637 B2
(45) Date of Patent: Aug. 30, 2016

(54) INTERVENTIONAL MR IMAGING WITH MOTION COMPENSATION

(75) Inventors: Sascha S. Krueger, Hamburg (DE); Steffen Weiss, Hamburg (DE); Bernd David, Huettblek (DE); Oliver Lips, Hamburg (DE); Robert Manzke, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 315 days.

(21) Appl. No.: 13/266,261

(22) PCT Filed: Apr. 14, 2010

(86) PCT No.: PCT/IB2010/051599
§ 371 (c)(1),
(2), (4) Date: Dec. 13, 2011

(87) PCT Pub. No.: WO2010/125486
PCT Pub. Date: Nov. 4, 2010

(65) Prior Publication Data
US 2012/0070056 A1    Mar. 22, 2012

(30) Foreign Application Priority Data
Apr. 28, 2009 (EP) .................................. 09158905

(51) Int. Cl.
*A61B 5/055* (2006.01)
*G01R 33/567* (2006.01)
(Continued)

(52) U.S. Cl.
CPC ........... *G01R 33/5673* (2013.01); *A61B 5/055* (2013.01); *A61B 5/064* (2013.01); *A61B 5/7207* (2013.01); *G01R 33/287* (2013.01); *G01R 33/4824* (2013.01); *G01R 33/56509* (2013.01)

(58) Field of Classification Search
CPC .... A61B 5/055; A61B 5/064; A61B 5/7207; G01R 33/287; G01R 33/4824; G01R 33/56509; G01R 33/5673
See application file for complete search history.

(56) References Cited

U.S. PATENT DOCUMENTS 6,171,240 B1 * 1/2001 Young et al. ................. 600/410
8,155,417 B2 * 4/2012 Piron et al. ................... 382/131
(Continued)

FOREIGN PATENT DOCUMENTS

WO    WO2009024898    2/2009

OTHER PUBLICATIONS

A.J. Kiruluta et al., "Motion Correction in High-Resolution Coronary MRI Using Measurements from In-Situ Tracking and Imaging Catheters", Proc. intl. Soc. Mag Reson. Med. 13 (2005), p. 511.
(Continued)

*Primary Examiner* — Ruth S Smith

(57) ABSTRACT

A method of magnetic resolution (MR) imaging of a moving portion of a body of a patient placed in an examination volume of a MR device. For the purpose of enabling improved interventional MR imaging from acquiring a MR signal data with motion compensation, the invention proposes that the method includes repeated acts of collecting tracking data from an interventional instrument introduced into the portion of the body, subjecting the portion of the body to an imaging sequence for acquiring one or more MR signals therefrom, wherein parameters of the imaging sequence are adjusted on the basis of the tracking data, and reconstructing one or more MR images from the MR signal data set.

10 Claims, 2 Drawing Sheets

(51) Int. Cl.
*A61B 5/06* (2006.01)
*A61B 5/00* (2006.01)
*G01R 33/28* (2006.01)
*G01R 33/48* (2006.01)
*G01R 33/565* (2006.01)

(56) References Cited

U.S. PATENT DOCUMENTS

2005/0054913 A1   3/2005   Duerk et al.
2005/0054914 A1   3/2005   Duerk et al.
2006/0074296 A1   4/2006   Dumoulin et al.
2008/0097189 A1   4/2008   Dumoulin et al.
2008/0114235 A1   5/2008   Unal et al.
2008/0161678 A1*  7/2008   Miyazaki et al. ............ 600/419

OTHER PUBLICATIONS

J. Curcic et al., "144 Prospective Self-Gating for Simultaneous Compensation of Cardiac and Respiratory Motion", Journal of Cardiovascular Magnetic Resonance, 11th Annual SCMR Scientific Sessions, Los Angeles, CA, USA, Feb. 1-3, 2008, pp. 1-4.

Y. Feng et al., "Improved Algorithms for Motion Estimation in the Reconstruction of Propeller MRI Data", IEEE, pp. 744-747.

* cited by examiner

INTERVENTIONAL MR IMAGING WITH MOTION COMPENSATION

FIELD OF THE INVENTION

The invention relates to the field of magnetic resonance (MR) imaging. It concerns a method of MR imaging of at least a moving portion of a body of a patient placed in an examination volume of an MR device. The invention also relates to an MR device and to a computer program to be run on an MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The signal data obtained via the receiving coils corresponds to the spatial frequency domain and is called k-space data. The k-space data usually includes multiple lines acquired with different phase encoding. Each line is digitized by collecting a number of samples. A set of k-space data is converted to an MR image, e.g., by means of Fourier transformation.

Cardiac interventional MR imaging is a promising tool in which accurate localization of an interventional instrument with excellent soft tissue contrast can be combined. Moreover, functional information from the heart can be obtained by means of appropriate MR imaging techniques. The combination of MR imaging with tracking of interventional instruments is especially advantageous for therapeutic applications that require therapy monitoring, like, e.g., MR electrophysiology interventions. However, cardiac MR imaging is associated with a compromise between spatial resolution, scan time and signal-to-noise ratio (SNR). Therefore effective motion compensation is of utmost importance. Acquisition of sufficient MR data for reconstruction of an image takes a finite period of time. Motion of the object to be imaged, like the beating motion of the heart in combination with the respiratory motion of the patient, during that finite acquisition time typically results in motion artifacts in the respective reconstructed MR image. The acquisition time can be reduced to a very small extend only, when a given resolution of the MR image is specified. In dynamic MR imaging scans, as required for therapy monitoring, the motion of the examined object during data acquisition leads to different kinds of blurring, mispositioning and deformation artifacts. Prospective motion correction techniques, such as the so called navigator technique or PACE, have been developed to overcome problems with respect to motion by prospectively adjusting the imaging parameters, i.e. the parameters of the imaging sequence used for MR signal acquisition, which define the location and orientation of the field of view (FOV) within the imaging volume. In the navigator technique, a MR data set is acquired from a pencil-shaped volume (navigator beam) that crosses the diaphragm of the examined patient. The volume is interactively placed in such a way that the position of the diaphragm can be reconstructed from the acquired MR data set and used for motion correction of the FOV in real time. The navigator technique is primarily used for minimizing the effects of breathing motion in cardiac examinations. Opposed to the navigator technique, which requires a navigator beam to detect motion differences, the above-mentioned PACE technique uses previously acquired dynamic images to prospectively adjust the imaging parameters on the time scale of successive dynamic scans. Moreover, it is known to apply ECG-based gating for the purpose of synchronization of the image acquisition with the beating motion of the heart, thereby reducing motion artifacts due to cardiac cycling.

The known approaches of motion compensation disadvantageously require an increased scan time due to the decreased scan duty cycle. Moreover, the above-mentioned navigator technique requires complex scan planning.

On the other hand, it has recently been shown that MR imaging is capable of visualizing the effect of a cardiac electrophysiology ablation shortly after the ablation, wherein it was demonstrated that ablation-related physiologic changes can be identified by means MR imaging in-situ. However, presently limitations exist with respect to image quality due to limited SNR and motion artifacts.

SUMMARY OF THE INVENTION

From the foregoing it is readily appreciated that there is a need for an improved method of interventional MR imaging. It is consequently an object of the invention to enable MR monitored therapy of moving body portions without the need of ECG gating, navigator techniques or other time-consuming or complex methods of motion compensation.

In accordance with the present invention, a method of MR imaging of a moving portion of a body of a patient placed in an examination volume of a MR device is disclosed. The method comprises the steps of:
a) collecting tracking data from an interventional instrument introduced into the portion of the body,
b) subjecting the portion of the body to an imaging sequence for acquiring one or more MR signals therefrom, wherein parameters of the imaging sequence are adjusted on the basis of the tracking data,
c) acquiring a MR signal data set by repeating steps a) and b) several times,
d) reconstructing one or more MR images from the MR signal data set.

The method of the invention allows the acquisition of motion compensated MR images at the position of an interventional instrument which has been introduced into the respective moving portion (such as, e.g., the heart) of the body of the patient. The gist of the invention is using the tracking data, i.e. the localization information collected from the interventional instrument, for intra-image motion compensation. The interventional instrument preferably comprises active means for tracking so as to report its position and orientation within the examined portion of the body to the MR device used for imaging. Known active MR tracking techniques, which utilize one or more RF micro coils attached to the interventional instrument, are well suited for the method of the invention. However, known passive markers, which can be used in MR imaging in combination with suitable detection algorithms, are also feasible. Other non-MR based tracking techniques may be used as well. In this case, an appropriate interface between the respective tracking system and the MR device is required in order to enable the integration of the tracking data into the sequence control of the MR device.

Preferably, the tracking data collected in accordance with the present invention comprises information as to the momentary position (x, y, z coordinates) and/or orientation (Euler angles) of at least a portion of the interventional instrument (e.g. catheter tip) within the examination volume. In case of RF micro coils attached to the interventional instrument the respective RF micro coils are preferably connected to the MR device via an appropriate transmission line (RF, optical or wireless). Appropriate interfaces for integrating such MR-based tracking into MR imaging methods are as such known in the art (see, e.g., US 2008/0097189 A1). In this way, the MR device includes appropriate software implementing imaging sequences to acquire the MR signals and to collect and evaluate the micro coil coordinates.

In the method of the invention, as mentioned above, the examined moving portion of the body is subjected to an imaging sequence for acquiring MR signals for image reconstruction, wherein parameters of the imaging sequence are adjusted on the basis of the tracking data. This means, that the MR device adapts the scan parameters on the basis of the tracking data, thereby causing a shift and/or a rotation of the scan geometry in accordance with the examined moving anatomy in real time. This adjustment of imaging parameters can be applied in accordance with the invention even for individual k-space lines. The adjustment of imaging parameters during the MR signals acquisition enables a prospective correction of arbitrary motion in the proximity of the interventional instrument. The approach of the invention is considered especially useful for MR monitored therapies, such as, e.g., catheter ablation. The invention makes use of the position information included in the tracking data from the interventional instrument which stays in a fixed geometrical relation to the anatomy.

In accordance with a preferred embodiment of the invention, a dynamic series of MR images is reconstructed from repeatedly acquired MR signal data sets. This means, that 4D MR imaging is carried out, wherein the parameters of the imaging sequence are continuously adapted on the basis of the collected tracking data, such that the FOV is kept essentially in a temporally constant geometrical relationship with respect to the examined moving portion of the body.

If the interventional instrument unintentionally 'slips', i.e. moves in relation to the anatomy to be imaged and/or treated, an immediate increase of motion artifacts in the MR images reconstructed in accordance with the invention occurs. These artifacts can be detected automatically and a corresponding warning to the user of the MR device and/or to the interventionalist can be generated.

Alternatively, motion of the interventional instrument relative to the moving portion of the body can be identified in accordance with the invention by detection of a deviation of the motion of the interventional instrument from a repetitive motion pattern on the basis of the repeatedly collected tracking data. Also this way of detection of 'slips' of the interventional instrument can be used for generation of a warning to the interventionalist.

The method of the invention thus advantageously enables the automatic detection of improperly fixed positioning of a therapeutic or diagnostic interventional device with respect to the anatomy to be treated and/or examined, thereby improving the accuracy of the treatment and, consequently, the result of the treatment. For these reasons, the method of the invention is particularly advantageous for interventional cardiac MR imaging, wherein trackable catheter-like devices are used. An experienced interventionalist is able to firmly fix the interventional instrument with respect to the local cardiac anatomy to either apply a therapy or to perform a certain diagnosis. The tracked interventional instrument than immediately can be used to detect the local motion of the cardiac anatomy very accurately and with high temporal resolution. According to the invention, this tracking data allows to perform an intra-image prospective motion correction, i.e. per acquisition of individual k-space lines or segments, and therefore enables the acquisition of motion compensated MR signals without the need for navigating, ECG triggering or other motion estimation and/or compensation techniques. In this way, faster MR imaging of local anatomy is allowed for, which can be used for increasing the SNR with concurrently reduced motion artifacts. In case of an actively tracked ablation catheter, lesion scanning can be performed effectively without any geometry planning, since the interventional instrument is located right at the lesion and thus can be used directly to define the FOV. This can be extremely useful for creation of repeated point-like ablations, e.g. for the purpose of creating a connected ablation ring or line, as required for pulmonary vein isolation. At the same time, the accuracy of the treatment is significantly improved since unintentional 'slips' of the instrument relative to the anatomy to be treated are immediately and reliably recognized due to the principle of the invention.

The method of the invention can advantageously be combined with PROPELLER imaging. In the known PROPELLER concept (periodically rotated overlapping parallel lines with enhanced reconstruction), the MR signals are acquired in k-space in N strips, each consisting of L parallel lines, corresponding to the L lowest frequency phase encoding lines in a cartesian k-space sampling scheme. Each strip, which is also referred to as k-space blade, is rotated in k-space by an angle 180°/N, so that the total MR data set spans approximately a circle in k-space. One essential characteristic of PROPELLER is that a central circular portion in k-space, having a diameter L is acquired for each k-space blade. This central portion can be used to reconstruct a low-resolution image for each k-space blade. These low-resolution images, or their k-space representations, can be compared to each other to remove in-plane displacements and phase errors, which are due to motion of the examined object. In addition, a suitable technique such as cross-correlation can be employed to determine which k-space blades were acquired with significant through-plane displacement. As the MR signals are combined in k-space before the reconstruction of the final MR image, MR data from k-space blades with the least amount of through-plane motion are preferentially used in regions in which the k-space blades overlap, so that artifacts arising from through-plane motion are reduced. The PROPELLER approach makes use of oversampling in the central portion of k-space in order to obtain an MR image acquisition technique that is robust with respect to motion of the examined body portion. The method of the invention can be used to adjust the position and/or angulation of the individual k-space blades of the PROPELLER sequence on the basis of the collected tracking data. An extremely accurate motion correction is achieved in this way by combination of correlation of the redundant center of k-space data with the collected tracking data from the interventional instrument which is fixed relative to the examined anatomy.

The method of the invention described thus far can be carried out by means of an MR device including at least one main magnet coil for generating a uniform, steady magnetic field within an examination volume, a number of gradient coils for generation of switched magnetic field gradients in different spatial directions within the examination volume, at least one RF coil for generating RF pulses within the examination volume and for receiving MR signals from a body of a patient positioned in the examination volume, a control unit for controlling the temporal succession of RF pulses and switched magnetic field gradients, a reconstruction unit, and a visualization unit. For enabling collection of tracking data from an interventional instrument in accordance with the invention, a suitable instrument tracking system should be connected to the MR device. For active MR-based tracking, at least one RF micro coil may be attached to the interventional instrument, wherein the tracking data is collected via the MR device as MR signals generated or picked up by the RF micro coil.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings

DETAILED DESCRIPTION

Figure 1:
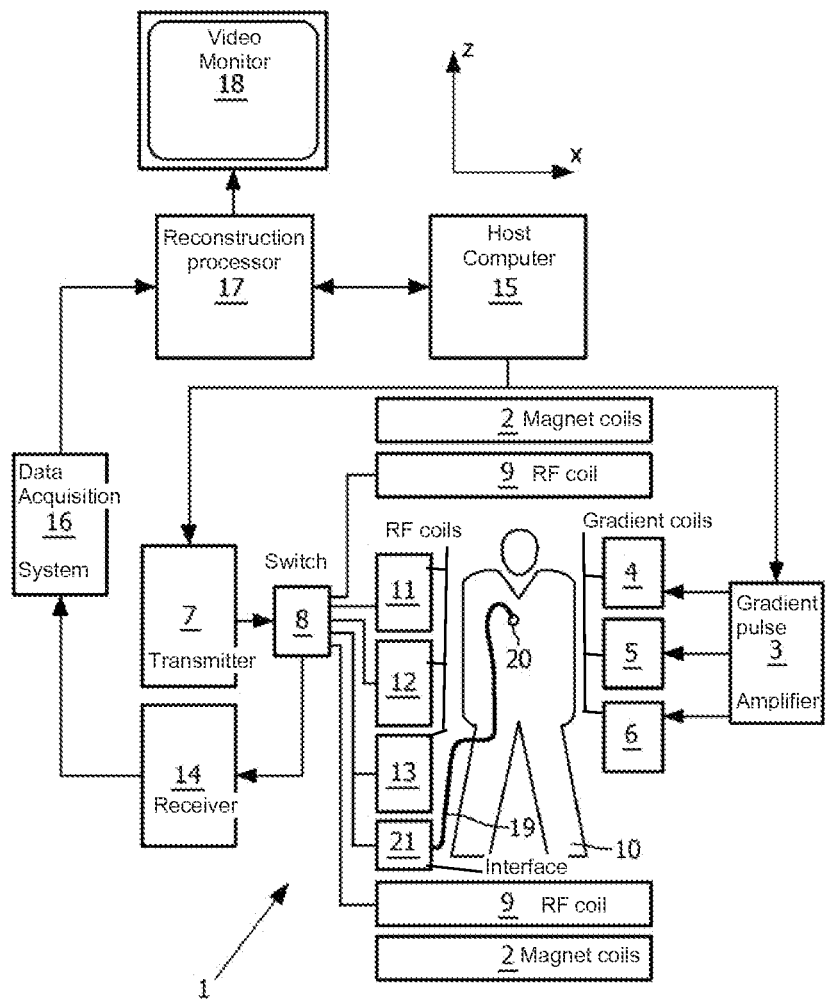
FIG. 1 shows a MR device for carrying out the method of the invention.

With reference to FIG. 1, a MR device 1 is shown. The device comprises superconducting or resistive main magnet coils 2 such that a substantially uniform, temporally constant main magnetic field is created along a z-axis through an examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

More specifically, a gradient pulse amplifier 3 applies current pulses to selected ones of whole-body gradient coils 4, 5 and 6 along x, y and z-axes of the examination volume. A digital RF transmitter 7 transmits RF pulses or pulse packets, via a send-/receive switch 8, to a whole-body volume RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the whole-body volume RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions.

The resultant MR signals picked up by the whole body volume RF coil 9 and/or by the array RF coils 11, 12, 13 are demodulated by a receiver 14 preferably including a pre-amplifier (not shown). The receiver 14 is connected to the RF coils 9, 11, 12 and 13 via send-/receive switch 8.

A host computer 15 controls the gradient pulse amplifier 3 and the transmitter 7 to generate any of a plurality of MR imaging sequences, such as turbo spin echo (TSE) imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE or SMASH. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

An interventional instrument 19, such as, e.g., an ablation catheter, is introduced into the body 10 of the patient. The catheter 19 is connected to the receiving chain of the MR device 1 via an interface 21. A RF micro coil 20 is attached to the distal end of catheter 19, thereby enabling the localization of the catheter tip by picking up MR signals via the RF micro coil 20 in the presence of magnetic field gradients.

Figure 2:
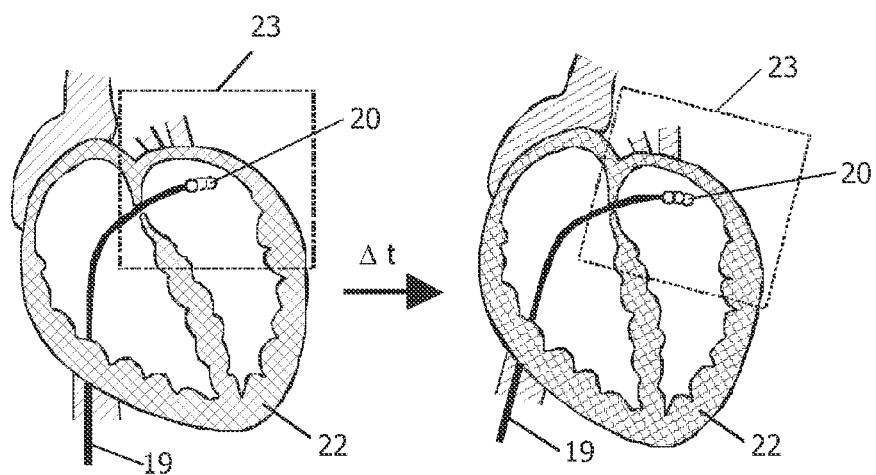
FIG. 2 schematically shows a moving heart of a patient examined in accordance with the method of the invention.

With reference to FIG. 2, a schematic cut-away view of a heart 22 of the patient is shown at two different instances separated by a time interval Δt. The ablation catheter 19 is introduced into the heart 22, wherein the catheter tip, to which the micro coil 20 is attached, is firmly fixed to the myocardium. Since the tip of the catheter 19 stays in a locally fixed relation to the anatomy of the heart, the position information derived from the tracking data collected via the micro coil 20 is used in accordance with the invention to adapt the scanning parameters of the imaging sequence in order to achieve a motion correction of the FOV 23 in real time. FIG. 2 shows that the FOV 23 has changed its position and orientation during the time interval Δt. The actively-tracked ablation catheter 19 is in this way used to detect the local motion of the anatomy for performing an intra-image prospective motion correction. The FOV 23 is translated and rotated so that it remains in a fixed geometrical relationship with respect to the examined anatomy of the heart 22. No navigator gating, ECG gating or other motion compensation techniques are required. The lesion generated by ablation catheter 19 can directly be scanned at high image quality, i.e. without motion artifacts due to breathing motion and/or beating motion of the heart 22. If the catheter 19 'slips' such that catheter 19 moves in relation to the anatomy of the heart 22, an immediate increase of motion artifacts will occur in the MR image reconstructed from the acquired MR signals. This is because the anatomy stays no longer in a fixed geometrical relation with respect to the FOV 23. The sudden increase of image artifacts can be used to generate a corresponding warning to the interventionalist.

The invention claimed is:

1. A method of magnetic resonance (MR) imaging of a moving portion of a body of a patient in an examination volume of a MR device, the method comprising acts of:
fixing the moving portion of the body to an instrument comprising a micro coil configured to generate tracking signals;
acquiring MR signal data producing an MR signal data set by repeatedly
generating tracking signals by the micro coil of the instrument,
deriving translation and/or rotation parameters describing motion of the moving portion of the body from the generated tracking signals,
adjusting imaging parameters to compensate for the motion of the moving portion of the body using the derived translation and/or rotation parameters,
subjecting the moving portion of the body to an MR imaging sequence using the adjusted imaging parameters, and acquiring one or more MR signals in response to the MR imaging sequence and thereby producing the MR signal data set; and
reconstructing one or more MR images from the produced MR signal data set.

2. The method of claim 1, wherein the act of adjusting comprising an act of maintaining a field of view in a temporally constant geometrical relationship with respect to the moving portion of the body.

3. The method of claim 1, wherein a dynamic series of MR images is reconstructed from the acquired MR signal data.

4. The method of claim 1, further comprising acts of:
detecting motion artefacts within a reconstructed MR image; and
identifying motion of the instrument relative to the moving portion of the body using the detected motion artefacts within the reconstructed MR image.

5. The method of claim 1, further comprising acts of:
detecting a deviation of the motion of the instrument from a repetitive motion pattern on a basis of the collected tracking signals; and
identifying motion of the instrument relative to the moving portion of the body using the detected deviation of the motion of the instrument from the repetitive motion pattern.

6. The method of any claim 1, wherein the act of subjecting the moving portion of the body to an imaging sequence comprises an act of subjecting the moving portion of the body to periodically rotated overlapping parallel lines with enhanced reconstruction (PROPELLER) sequence; and the act of adjusting adjusts position and/or angulation of individual k-space blades of the PROPELLER sequence on a basis of the generated tracking signals.

7. A magnetic resonance (MR) device comprising:
at least one main magnet coil for generating a uniform, steady magnetic field within an examination volume;
a plurality of gradient coils for generating switched magnetic field gradients in different spatial directions within the examination volume;
at least one RF coil for generating RF pulses within the examination volume and/or for receiving MR signals from a body of a patient positioned in the examination volume;
a controller configured to control the temporal succession of RF pulses and switched magnetic field gradients; and
a processor configured to control the MR device to acquire MR signal data producing an MR signal data set by repeatedly
generating tracking signals by a micro coil of an instrument fixed to a moving portion of the body of the patient,
deriving translation and/or rotation parameters describing motion of the moving portion of the body from the generated tracking signals
adjusting imaging parameters producing dusted imaging parameters to compensate for the motion of the moving portion of the body using the derived translation and/or rotation parameters, and
subjecting the moving portion of the body to an MR imaging sequence comprising RF pulses generated via the RF coil and switched magnetic field gradients generated via the gradient coils using the adjusted imaging parameters; and
reconstructing one or more MR images from the produced MR signal data set.

8. The MR device of claim 7, wherein the micro coil is at least one RF micro coil.

9. The MR device of claim 7, further comprising a system for collecting the tracking signals.

10. A computer readable non-transitory medium comprising a program which when executed on a magnetic resonance (MR) imaging device performs a method of MR imaging of a moving portion of a body of a patient placed in an examination volume of a MR device, the method comprising acts of:

acquiring MR signal data by repeatedly
generating tracking signals from a micro coil of an instrument fixed to the moving portion of the body,
deriving translation and/or rotation parameters describing motion of the moving portion of the body from the generated tracking signals,
adjusting imaging parameters producing adjusted imaging parameters to compensate for the motion of the moving portion of the body using the derived translation and/or rotation parameters, and
generating an imaging sequence and subjecting the moving portion of the body to the imaging sequence comprising a plurality of pulses and switched magnetic field gradients using the adjusted imaging parameters; and
reconstructing one or more MR images from the acquired MR signal data.

\* \* \* \* \*